US006844409B2

(12) United States Patent
Angeletakis et al.

(10) Patent No.: US 6,844,409 B2
(45) Date of Patent: Jan. 18, 2005

(54) COMPOSITION CURABLE BY METATHESIS REACTION

(75) Inventors: Christos Angeletakis, Orange, CA (US); Mingfei Chen, Santa Rosa, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 10/430,953

(22) Filed: May 6, 2003

(65) Prior Publication Data

US 2003/0212233 A1 Nov. 13, 2003

Related U.S. Application Data

(60) Provisional application No. 60/380,154, filed on May 6, 2002.

(51) Int. Cl.[7] .............................................. C08G 77/08
(52) U.S. Cl. ........................ 526/279; 526/171; 528/15; 528/32
(58) Field of Search ..................... 528/15, 32; 526/279, 526/171

(56) References Cited

U.S. PATENT DOCUMENTS

| | | | |
|---|---|---|---|
| 4,717,498 A | 1/1988 | Maxon | 252/174.15 |
| 4,849,127 A | 7/1989 | Maxon | 252/174.15 |
| 5,198,511 A | 3/1993 | Brown-Wensley et al. | 526/113 |
| 5,266,670 A | 11/1993 | Nakos et al. | 528/32 |
| 5,296,566 A | 3/1994 | Brown-Wensley et al. | 526/171 |
| 5,312,881 A | 5/1994 | Marks et al. | 526/126 |
| 5,330,948 A | 7/1994 | Marks et al. | 502/104 |
| 5,455,317 A | 10/1995 | Marks et al. | 526/126 |
| 5,491,206 A | 2/1996 | Brown-Wensley et al. | 526/126 |
| 5,728,785 A | 3/1998 | Grubbs et al. | 526/142 |
| 5,831,108 A | 11/1998 | Grubbs et al. | 556/21 |
| 5,939,504 A | 8/1999 | Woodson, Jr. et al. | 526/145 |
| 5,942,638 A * | 8/1999 | Lichtenhan et al. | 556/460 |
| 6,001,909 A | 12/1999 | Setiabudi | 524/265 |
| 6,040,363 A | 3/2000 | Warner et al. | 523/214 |
| 6,071,459 A | 6/2000 | Warner et al. | 264/311 |
| 6,075,068 A | 6/2000 | Bissinger | 523/116 |
| 6,077,805 A | 6/2000 | Van Der Schaaf et al. | 502/155 |
| 6,121,362 A | 9/2000 | Wanek et al. | 524/448 |
| 6,252,101 B1 | 6/2001 | Herzig et al. | 556/453 |
| 6,306,987 B1 | 10/2001 | Van Der Schaaf et al. | 526/171 |
| 6,310,121 B1 | 10/2001 | Woodson, Jr et al. | 524/32 |
| 6,323,296 B1 | 11/2001 | Warner et al. | 526/171 |
| 6,403,522 B1 | 6/2002 | Bolm et al. | 502/155 |
| 6,407,190 B1 | 6/2002 | Van Der Schaaf et al. | 526/171 |
| 6,409,875 B1 | 6/2002 | Giardello et al. | 156/334 |
| 6,410,666 B1 | 6/2002 | Grubbs et al. | 526/171 |
| 6,417,363 B1 | 7/2002 | Van Der Schaaf et al. | 546/6 |
| 6,455,029 B1 * | 9/2002 | Angeletakis et al. | 424/49 |
| 6,465,554 B1 | 10/2002 | Van Der Schaaf et al. | 524/403 |
| 6,521,799 B2 * | 2/2003 | Wagener et al. | 568/852 |
| 6,525,125 B1 | 2/2003 | Giardello et al. | 524/439 |
| 6,620,955 B1 * | 9/2003 | Pederson et al. | 556/21 |
| 6,649,146 B2 * | 11/2003 | Angeletakis et al. | 424/49 |
| 2002/0107138 A1 | 8/2002 | Hoveyda et al. | 502/152 |
| 2002/0137978 A1 | 9/2002 | Grubbs et al. | 585/507 |
| 2002/0153096 A1 | 10/2002 | Giardello et al. | 156/334 |
| 2002/0185630 A1 | 12/2002 | Piccinelli et al. | 252/184 |

FOREIGN PATENT DOCUMENTS

| | | | |
|---|---|---|---|
| EP | 0796607 | 9/1997 | A61K/6/00 |
| EP | 0771830 | 12/1999 | C08K/5/32 |
| EP | 1025830 | 9/2000 | A61K/6/087 |
| EP | 1241196 | 9/2002 | C08F/293/00 |
| WO | WO 98/39346 | 9/1998 | C07F/15/00 |
| WO | WO 99/00396 | 1/1999 | C07F/15/00 |
| WO | WO 99/00397 | 1/1999 | C07F/15/00 |
| WO | WO 99/29701 | 6/1999 | C07F/15/00 |
| WO | WO 99/50330 | 10/1999 | C08G/61/00 |
| WO | WO 99/60030 | 11/1999 | C08F/4/20 |
| WO | WO 00/46255 | 8/2000 | C08F/4/80 |

OTHER PUBLICATIONS

International Organization for Standardization, *Dental Elastomeric Impression Materials*, ISO 4823 (1992).

Scholl et al., *Synthesis and Activity of a New Generation of Ruthenium–Based Olefin Metathesis Catalysts Coordinated with 1,3–Dimesityl–4,5–dihydroimidazol–2–ylidene Ligands*, Org. Lett., vol. 1, No. 6, 953–956 (1999).

Chevaller et al., *Ring–Opening Olefin Metathesis Polymerisation (ROMP) as a Potential Cross–Linking Mechanism for Siloxane Polymers*, J. of Inorganic and Organometallic Polymers, vol. 9, No. 3, 151–164 (1999).

L. LeCamp et al., *Polydimethyl siloxane photoreticulable par voie cationique–I*, Eur. Polym. J. vol. 33, No. 9, pp. 1453–1462 (1997).

Kim et al., *Surface–Initiated Ring–Opening Metathesis Polymerization on Si/SiO2*, Macromolecules 2000, 33(8), 2793–2795.

* cited by examiner

Primary Examiner—Margaret G. Moore
(74) Attorney, Agent, or Firm—Wood, Herron & Evans, LLP

(57) ABSTRACT

A composition curable by a metathesis reaction and comprising an olefin-containing resin system and metathesis catalyst. The resin system comprises siloxane-based oligomers or polymers end-capped and/or tethered with olefin functional groups that are capable of undergoing a metathesis reaction. The composition also includes a ruthenium carbene complex catalyst, whereby the catalyst initiates the metathesis reaction of the composition. The oligomer or polymer may be, for example, one or a combination of a telechelic polydimethylsiloxane end-capped with norbornenylethyl groups, a polydimethylsiloxane tethered and end-capped with norbornenylethyl groups, a tri-functional polydimethylsiloxane end-capped with norbornenylethyl groups, or a quadri-functional polydimethylsiloxane end-capped with norbornenylethyl groups. The catalyst may be, for example, a ruthenium carbene complex, such as 1,3-bis-(2,4,6-trimethylphenyl)-2-(imidazolidinylidene) dichloro(o-isopropoxyphenylmethylene) ruthenium.

41 Claims, No Drawings

COMPOSITION CURABLE BY METATHESIS REACTION

CROSS REFERENCE TO RELATED APPLICATIONS

This application claims the benefit of and priority to prior filed co-pending Provisional Application Ser. No. 60/380,154, filed May 6, 2002, which is expressly incorporated herein by reference. This application is related to co-pending, commonly-owned U.S. patent application Ser. No. 10/430,592 entitled METATHESIS-CURABLE COMPOSITION WITH A REACTION CONTROL AGENT and Ser. No. 10/430,590 entitled METHOD OF CURING COMPOSITION BY METATHESIS REACTION USING REACTION CONTROL AGENT, both tiled on even date herewith, and to co-pending, commonly-owned U.S. patent application Ser. No. 10/010,777 filed Dec. 6, 2001, now U.S. Pat. No. 6,649,146 and entitled DENTAL IMPRESSION MATERIAL UTILIZING RUTHENIUM METATHESIS CATALYST, which is a continuation-in-part of U.S. Pat. No. 6,455,029 issued Sep. 24, 2002 and entitled DENTAL IMPRESSION MATERIAL UTILIZING RUTHENIUM CATALYST, the disclosures of which are incorporated herein by reference in their entirety as if completely set forth herein below. This application is also related to co-pending, commonly-owned, U.S. patent application Ser. No. 10/313,359, which claims the benefit of Provisional U.S. Patent Application Ser. No. 60/338,439 filed Dec. 6, 2001, both entitled ACCELERATOR FOR METATHESIS CATALYST, the disclosures of which are incorporated herein by reference in their entirety as if completely set forth herein below.

FIELD OF THE INVENTION

This invention relates to compositions that undergo a metathesis reaction initiated by a metathesis catalyst, and more particularly, to compositions curable by ring-opening metathesis polymerization with ruthenium complex catalysts.

BACKGROUND OF THE INVENTION

Addition polymerizable silicone resins are widely used in many fields such as electronics, health care and automotive applications. The polymerizable resins are cured as a two-part system using a hydrosilation reaction. A platinum catalyst is used in one part, the catalyst side, and a hydrogen terminated polydimethylsiloxane (HPDMS) in the other part, the base side, while both sides contain vinyl terminated polydimethylsiloxanes (PVDMS) resins. When these materials are cured at room temperature, they are referred to as room temperature vulcanized (RTV). The most common RTV materials are typically offered as a 10:1 ratio base/catalyst, such as RTV630 (GE Silicones), while some other RTV materials are offered at a 1:1 ratio, such as RTV6428 (GE Silicones). Various working times are required depending on the application from 2 minutes to several hours. The working time is controlled with a retarder or inhibitor mixed with the catalyst component, such as an amine or acetylenic compound.

Another class of addition polymerizable silicone resins are the liquid silicone rubber (LSR) materials prepared through the liquid injection molding (LIM) process. The LSR materials are cured at a temperature of 120° C.–180° C. in a mold injected to after mixing. The mixture includes a retarder mixed with the catalyst component, such as an amine or acetylenic compound, that allows the hydrosilation reaction to occur at the mold temperature only.

Both the RTV and LSR types of formulations suffer from the shortcomings of the hydrosilation mechanism. These shortcomings include: (1) deactivation of the platinum catalyst by sulfur or other nucleophilic impurities; (2) high shrinkage, approximately 1%, due to the high reduction of free volume upon polymerization; (3) high cost of platinum metal needed for catalysis; (4) high cost of HPDMS and PVDMS resins; (5) requirement of two different resins to be employed, namely vinyl and hydrogen terminated; (6) undesirable hydrogen evolution from the decomposition of the hydrosiloxane cross-linkers that typically are present in these systems; and (7) vinyl functionalized PDMS resins have a low hydrocarbon content in the main chain after polymerization due to the presence of only an ethyl spacer, which leads to a relatively high dielectric constant, which is an undesirable property for some electronic applications.

Another type of polymerization system has been recently developed, wherein curing is achieved by a ring-opening metathesis polymerization (ROMP) mechanism. Metathesis is generally understood to mean the metal catalyzed redistribution of carbon-carbon double bonds. The polymerizable composition comprises a resin system that includes functionalities or groups that are curable by ROMP together with a metathesis catalyst, such as a ruthenium carbene complex. Because the ROMP system is relatively new, there still exists a need to develop polymerizable compositions that cure efficiently by this metathesis reaction. This need includes more efficient resins and catalysts.

In addition to ROMP, other metathesis reaction systems utilize metathesis catalysts, for example ring closing metathesis, acyclic diene metathesis polymerization, ring opening metathesis and cross metathesis. There is further a need for increasing the efficiency of curing in these other metathesis reaction systems. Impression material used in dentistry is one application in which the metathesis reaction system may be used to replace addition-curable silicones. Dental impression materials comprising a polymerizable resin curable by ring-opening metathesis polymerization (ROMP), a dental filler system, and a ruthenium carbene complex catalyst, whereby the catalyst initiates the ring-opening metathesis polymerization of the composition, are described in commonly owned, co-pending U.S. patent application Ser. No. 10/010,777 filed Dec. 6, 2001, now U.S. Pat. No. 6,649,146, and entitled DENTAL IMPRESSION MATERIAL UTILIZING RUTHENIUM METATHESIS CATALYST and commonly owned U.S. Pat. No. 6,455,029 issued Sep. 24, 2002 and entitled DENTAL IMPRESSION MATERIAL UTILIZING RUTHENIUM CATALYST, each of which is incorporated herein by reference in its entirety as if completely set forth herein below. The polymerizable resins described therein comprise one or more oligomers or polymers that can be tethered and/or end-capped with functional groups such as cycloalkenyl groups that can undergo a metathesis reaction initiated by a ruthenium carbene complex. The resin is combined with a dental filler system that provides the uncured and cured compositions with properties that make them suitable for use in a dental impression application. However, the metathesis reaction system has applicability far beyond the dental field.

Thus, there is a need for efficient metathesis reaction systems that may be used to replace addition-curable silicones and platinum catalysts in a wide variety of applications to thereby avoid the shortcomings of the hydrosilation mechanism discussed above.

SUMMARY OF THE INVENTION

The present invention provides a composition curable by a metathesis reaction. In one embodiment of the present invention, the composition comprises an olefin-containing resin system comprising one or more oligomers or polymers having a majority (>50%) siloxane (Si—O—Si) backbone that can be tethered and/or end-capped with functional olefin groups such as cycloalkenyl groups that can undergo a metathesis reaction, and a ruthenium catalyst that is capable of initiating the metathesis reaction of the composition, such as a ring opening metathesis polymerization (ROMP), to form a cured article. The catalyst may be one of the following:

(a) 1,3-bis-(2,4,6-trimethylphenyl)-2-(imidazolidinyl-idene) dichloro(o-isopropoxyphenyl- methylene) ruthenium; and (b)

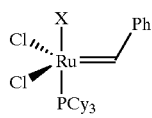

wherein Cy is cyclohexyl, Ph is phenyl and X is a saturated imidazole ligand having a basicity higher than tricyclohexylphosphine.

To phrase the resin system another way, the resin system may comprise one or a combination of the following: a telechelic siloxane-based oligomer or polymer end-capped with olefin groups capable of undergoing a metathesis reaction; a siloxane-based oligomer or polymer tethered and end-capped with olefin groups capable of undergoing a metathesis reaction; or a tri-functional or quadri-functional siloxane-based oligomer or polymer end-capped with olefin groups capable of undergoing a metathesis reaction. The main chain is advantageously a polydimethylsiloxane (PDMS). The functional olefin groups are advantageously norbornenylethyl (NBE) groups.

In an exemplary embodiment of the invention, the composition comprises an olefin-containing resin system comprising at least one oligomer or polymer having a polydimethylsiloxane backbone tethered and end-capped with norbornenylethyl groups capable of undergoing a metathesis reaction, and a ruthenium carbene complex catalyst, wherein the catalyst is capable of initiating the metathesis reaction in the composition to form a cured article. The catalyst is either a ruthenium carbene complex with at least one of the ligands being a saturated imidazole having a basicity higher than tricyclohexylphosphine, or a ruthenium carbene complex of the formula 1,3-bis-(2,4,6-trimethylphenyl)-2-(imidazolidinylidene) dichloro(o-isopropoxyphenyl-methylene) ruthenium.

The curable compositions of the present invention may be used in any application where compositions curable by the hydrosilation mechanism are used.

DETAILED DESCRIPTION

The present invention provides a composition having an olefin-containing resin system, such as a cyclic olefin-containing resin system or an acyclic olefin-containing resin system, in which the majority (>50%) of the backbone is siloxane, i.e., Si—O—Si, wherein the resin undergoes a metathesis reaction, such as ROMP, with the aid of a ruthenium carbene complex metathesis catalyst. The composition may comprise a catalyst paste and base paste in intimate admixture with one another in a polymerizable paste/paste system. Generally, in this system, the catalyst paste comprises the metathesis catalyst for initiating polymerization, and a solvent for the catalyst that is miscible or dispersible with the base paste. The base paste generally comprises an oligomer and/or polymer resin system that is curable via ROMP or other metathesis reaction. Advantageously, for a composition curable by ROMP, the resin system comprises at least one cyclic olefin functionalized majority siloxane oligomer or polymer that is telechelic, tethered, tri-functional or quadri-functional. More specifically, the resin system curable by ROMP may comprise one or a combination of the following: a polymerizable telechelic siloxane-based polymer end-capped with an olefin group curable by ROMP; a polymerizable siloxane-based polymer tethered and end-capped with an olefin group curable by ROMP; a polymerizable tri-functional siloxane-based oligomer or polymer end-capped with an olefin group curable by ROMP; and a polymerizable quadri-functional siloxane-based oligomer or polymer end-capped with an olefin group curable by ROMP.

By way of example and not limitation, one category of oligomers and/or polymers that may be used in compositions of the present invention include telechelic (end-functionalized/end-capped) polymers with any of a variety of backbones, comprising a majority (>50%) siloxane as long as the chain ends are functionalized with reactive olefin groups, such as cycloalkenyl groups. For example, the resin may be a telechelic PDMS terminated with NBE groups according the following structure:

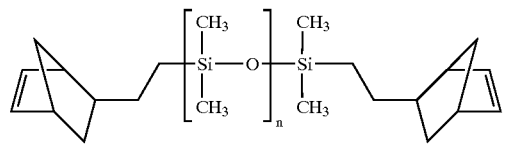

where n=5–5000, for example 27–1590. Other examples of telechelic polysiloxanes are those having the following structure:

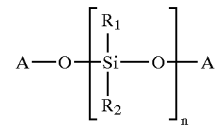

where n=5–5000, such as 27–1590;
$R_1$, $R_2$=$C_1$–$C_{18}$ hydrocarbon or

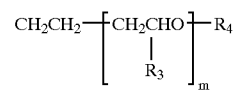

where $R_3$, $R_4$=H or $C_1$–$C_{18}$ hydrocarbon, and m=1–10; and

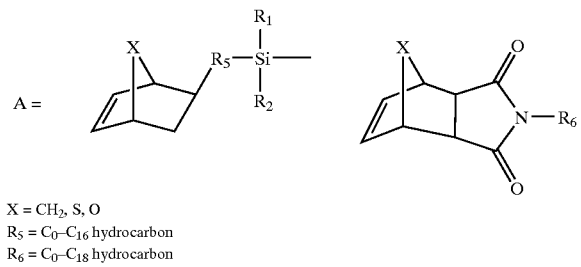

X = $CH_2$, S, O
$R_5$ = $C_0$–$C_{16}$ hydrocarbon
$R_6$ = $C_0$–$C_{18}$ hydrocarbon Another category of oligomers and/or polymers that may be used in compositions of the present invention include oligomers or polymers comprising a majority (>50%) siloxane tethered and end-capped with groups curable by a metathesis reaction, such as cycloalkenyl groups. The oligomers or polymers may have any of a variety of siloxane-based backbones, particularly PDMS, with pendant groups incorporated within the backbone or main chain that protrude therefrom thus forming the tethered structure. As with the telechelic polymers, the chain ends are functionalized or capped with reactive olefin groups, such as cycloalkenyl groups, for example norbornenyl or norbornenylethyl groups. The pendant groups may also be cycloalkenyl groups, such as norbornenyl or norbornenylethyl groups. For example, the resin may be a PDMS tethered and end-capped with NBE groups according the following structure:

bic substances and for improving the surface wettability. However, the addition of one or more surfactants to the compositions to obtain satisfactory water wettability of the cured composition may result in poor physical properties such as low tensile strength, elongation and tear strength. Nonetheless, the surfactants used can be cationic, anionic, amphoteric or nonionic. A nonionic-type surfactant is preferred, such as one comprising nonylphenoxy poly (ethyleneoxy) ethanol, available from Rhone-Poulenc, Cranbury, N.J., under the trade names IGEPAL® CO-520, CO-530 and the like. Alternatively, a silicone-based surfactant such as SILWET® 77 available from Witco Corp., Greenwich, Conn can be used.

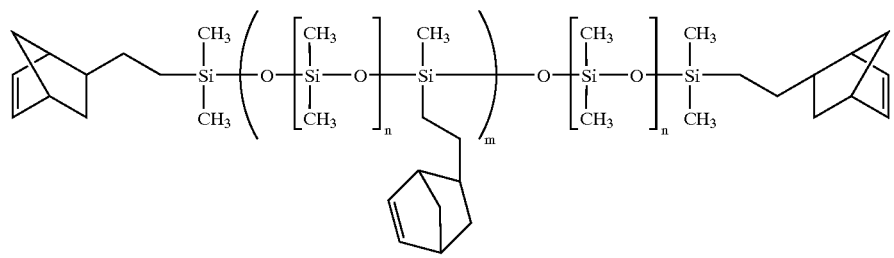

where n=5–5000, for example 27–1590, and m=1–100, for example 1–10. In an exemplary embodiment of the present invention, the resin system includes at least one PDMS tethered and end-capped with NBE groups.

Yet another category of oligomers and/or polymers that may be used in compositions of the present invention include tri- or quadri-functional oligomers or polymers having a majority (>50%) siloxane backbone end-functionalized or end-capped with an olefin group curable by a metathesis reaction, such as cycloalkenyl groups, for example norbornenyl or norbornenylethyl groups. An example of such polymer is quadri-functional PDMS, end-capped with NBE groups.

By way of example, the resin system may comprise both the telechelic oligomer or polymer and the tethered oligomer or polymer, each functionalized with groups curable by ROMP, or may comprise the telechelic oligomer or polymer and the tethered oligomer or polymer and the quadri-functional oligomer or polymer, each functionalized with groups curable by ROMP. Thus, the resin formulation may be varied to obtain desired physical properties in the uncured and cured material.

The cycloalkenyl functionalized PDMS resins that are cured via ROMP have a higher hydrocarbon content than the vinyl functionalized PDMS resins that are used in hydrosilation reactions. The higher hydrocarbon content leads to a lower dielectric constant, which is desirable for many electronic applications.

In addition to the above categories of oligomers and polymers, the resin system may comprise any other polymerizable cycloalkenyl-functionalized siloxane-based oligomers or polymers that may undergo polymerization via ROMP mechanism or any acyclic olefin-functionalized siloxane-based oligomer or polymer that may undergo acyclic diene metathesis polymerization. Other examples of reactive olefins include dicyclopentadiene or other cycloolefins.

A surfactant may be incorporated into the resin formulation, such as in the base paste. The inclusion of surfactants, including ionic- and nonionic-type surfactants, is known for imparting hydrophilic properties to hydropho- The catalysts useful in the present invention include ruthenium carbene complexes. The parent benzylidene ruthenium complex A, with the following structure, exhibits high air and water stability:

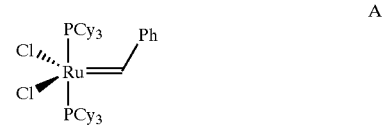

A wherein Cy is cyclohexyl and Ph is phenyl. The ring-opening metathesis activity of the parent complex A can be increased by substituting a saturated imidazole ligand X for a tricyclohexylphosphine ligand, in accordance with the following formula:

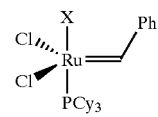

The ligands X may be 4,5-dihydroimidazol-2-ylidenes, which have the following general structure:

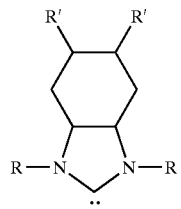

These substituted ligands X have a basicity higher than that of tricyclohexylphosphine, as indicated by a higher pKa, which is believed to contribute to the higher activity. Ruthenium complex B, a derivative of complex A and having the structure shown below, is a substituted ruthenium carbene complex including such a ligand:

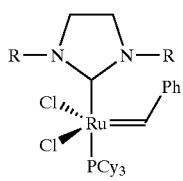

B wherein Cy is cyclohexyl, Ph is phenyl and R is mesityl. Other derivatives of parent complex A can also be used in the resin system of the composition of the present invention, such as substituted ruthenium carbene complexes C and D having the following structures:

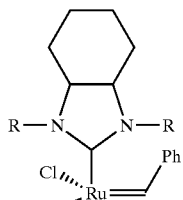

C

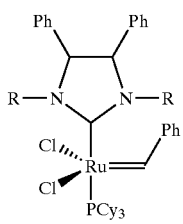

D wherein Cy is cyclohexyl, Ph is phenyl and R is mesityl. A new ruthenium carbene complex E was recently developed, and is commercially available from Aldrich Chemical Co. under product number 56,975-5. Specifically, complex E is 1,3-bis-(2,4,6-trimethylphenyl)-2-(imidazolidinylidene) dichloro(o-isopropoxyphenylmethylene) ruthenium having the following structure:

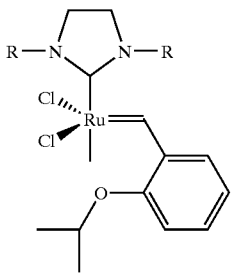

E wherein R is mesityl. In an exemplary embodiment, complex E is used with a resin system comprising ROMP curable NBE functionalized PDMS resins. The combination of this particular resin system and complex E is believed to provide a highly efficient metathesis reaction system.

The catalyst component of curable compositions of the present invention may be formulated by dissolving the ruthenium carbene complex in an inert solvent. The solvent, or diluent, is chosen such that the solvent and the complex are miscible (soluble) or dispersible with the base pastes, and such that the solvent does not interfere with the met- athesis reaction. The solvent may be, for example, 3-phenyl-heptamethyl-trisiloxane. Another exemplary solvent is a partially phenyl substituted poly(dimethylsiloxane), such as Dow Corning Fluid 556. The composition may further include filler systems and/or optional additives suitable for the particular application, such as pigments, that do not interfere with the reaction.

A catalyst accelerator may be incorporated into the resin formulation, such as in the base paste, to further accelerate the ROMP mechanism, thereby enhancing the efficiency of the ruthenium complex catalyst. Silicone-based sulfosuccinate salts act as accelerators for the ruthenium complex catalyst. While dimethicone copolyol sulfosuccinate is normally used as a surfactant for shampoos and the like, as fully described in U.S. Pat. Nos. 4,717,498 and 4,849,127, which are incorporated by reference herein in their entirety, it unexpectedly functions as a catalyst accelerator when used in formulations of the present invention containing the ruthenium complex catalysts, as set forth in co-pending, commonly-owned, U.S. Pat. application Ser. No. 10/313,359 and entitled ACCELERATOR FOR METATHESIS CATALYST, the disclosure of which is incorporated herein by reference in its entirety. An exemplary accelerator is DC-30A available from McIntyre Chemical Co., Chicago Ill.

EXAMPLE 1

A telechelic poly(dimethylsiloxane) end-capped with norbornenylethyl groups (Compound 1) was synthesized according to the following scheme using KOH as the acid scavenger:

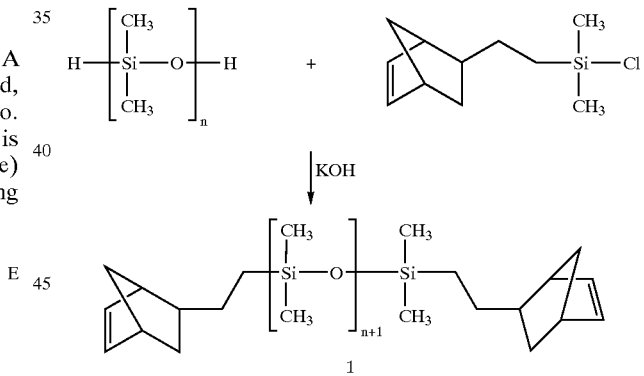

1

A 2L reaction kettle equipped with a mechanical stirrer, $N_2$ inlet-outlet and a thermal couple was charged with 900 g (0.06 mol, Polymer OH 0.75, Hans Chemie) silanol terminated poly(dimethylsiloxane) (PDMS). The system was cooled to 4° C. with an ice-water bath. Then, 25.78 g (0.12 mol) 2-(5-norbornenyl)ethyldimethylchlorosilane was added dropwise with a dropping funnel followed by 7.7 g (0.12 mol, 40 mesh, Aldrich Chemical, semiconductor grade, 87% purity) ground KOH and the reaction continued under stirring at ice-water temperature for three hours. The system was subjected to vacuum (about 2 torr) while the temperature was gradually raised to 80° C. over 30 minutes. The reaction continued at 80° C. for one hour under vacuum. A resin, Compound 1, was obtained with a viscosity of 1.4 Pa.s. The resin was allowed to stabilize at ambient temperature for one day to afford a product having a viscosity of 1.5 Pa.s., GPC (toluene) Mn 23,700 and Mw 41,400.

EXAMPLE 2

A poly(dimethylsiloxane) tethered and end-capped with norbornenylethyl groups (Compound 2) was synthesized according to the following scheme using KOH as acid scavenger:

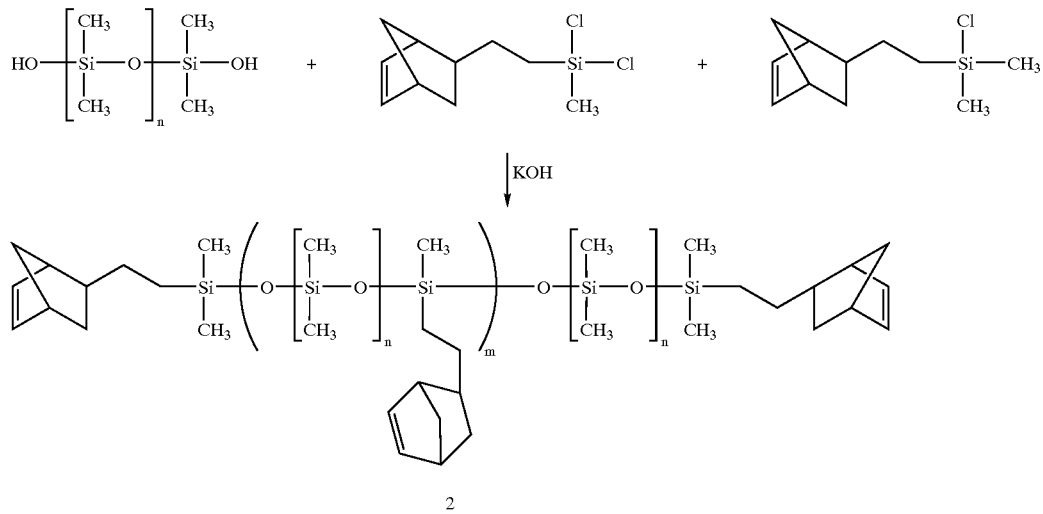

2

A 2L reaction kettle equipped with a mechanical stirrer, N₂ inlet-outlet and a thermal couple was charged with 900 g (0.06 mol, Polymer OH 0.75, Hans Chemie) silanol terminated poly(dimethylsiloxane) (PDMS). The system was cooled to 4° C. with an ice-water bath. Then, a mixture of 8.55 g (36.3 mmol) 2-(5-norbornenyl) ethylmethyldichlorosilane and 10.55 g (47.3 mmol) 2-(5-norbornenyl) ethyldimethylchlorosilane was added dropwise with a dropping funnel followed by 8.51 g (132 mmol, 40 mesh, Aldrich Chemical, semiconductor grade, 87% purity) ground KOH and the reaction continued under stirring at ice-water temperature for three hours. The system was subjected to vacuum (about 2 torr) while the temperature was gradually raised to 80° C. over 30 minutes. The reaction continued at 80° C. for one hour under vacuum. A resin, Compound 1, was obtained with a viscosity of 9.4 Pa.s. The resin was allowed to stabilize at ambient temperature for three days to afford a product having a viscosity of 17.4 Pa.s., GPC (toluene) Mn 55,000 and Mw 101,000.

EXAMPLE 3

A quadri-functional poly(dimethylsiloxane), referred to as a Q-resin, end-capped with norbornenylethyl groups (Compound 3) was synthesized according to the following scheme.

A 1L round bottom flask equipped with a Dean-Stark trap and a magnetic spin bar was charged with 50 g silanol terminated Q-resin (SQO—299, Mw 3000–4000, OH 1.7–2.0% from Gelest Corp.) dissolved in 250 mL toluene. The system was cooled to 0° C. with an ice-water bath. Then, 15.8 g (74 mmol) 2-(5-norbornenyl) ethyldimethylchlorosilane and 5.22 g (81 mmol, 40 mesh, Aldrich Chemical, semiconductor grade, 87% purity) ground KOH were added. The reaction continued under stirring at 0° C. for three hours. The reaction was stirred overnight at room temperature, then under reflux the water-azeotrope was removed. After cooling down, salts were removed by vacuum filtration and toluene was evaporated on a rotary evaporator to afford a semi-solid product, Compound 3. The yield was 97%. The results of NMR (Nuclear Magnetic Resonance) and GPC analysis are as follows: GPC (toluene) Mn 2,300 and Mw 3,000, NMR(1H) 0.15 δ (CH₃—Si), 5.9, 6.1 δ (vinyl H).

A base resin composition for use in the present invention may comprise, for example, the components listed in Table 1, in varying amounts, as shown.

TABLE 1

Base Resin Composition (wt. %)

| Base Resin | Resin 1 | Resin 2 | Resin 3 | Resin 4 | Resin 5 | Resin 6 |
|---|---|---|---|---|---|---|
| End-capped PDMS, 1 | 30 | 29.8 | 29.8 | 29.8 | 29.9 | 21 |
| Tethered PDMS, 2 | 70 | 70.12 | 69.45 | 59.55 | 69.7 | 74.25 |
| NBE Functionalized Q-resin, 3 | 0 | 0 | 0 | 9.9 | 0 | 4 |
| Accelerator (DC-30A)[1] | 0 | 0.08 | 0.25 | 0.25 | 0.15 | 0.25 |
| Surfactant (IGEPAL ® CO-520)[2] | 0 | 0 | 0.50 | 0.50 | 0.25 | 0.50 |

[1]A dimethicone copolyol sulfosuccinate ammonium salt available from McIntyre Chemical Co., Chicago IL.
[2]An ethoxylated alkylphenol available from Rhone-Poulenc, Cranberry NJ.

The catalyst used may be any of complexes A–E, for example 1,3-dimesityl-4,5-dihydroimidazol-2-ylidene-substituted ruthenium carbene complex (B) with the structure indicated above, obtained from Materia Inc., Pasadena, Calif. or 1,3-bis-(2,4,6-trimethylphenyl)-2-(imidazolidinylidene) dichloro(o-isopropoxyphenyl-methylene) ruthenium complex (E) with the structure indicated above, obtained from Aldrich Chemical Co. The catalyst paste may be formulated by dissolving the ruthenium carbene complex in a partially phenyl substituted poly(dimethylsiloxane), for example, Dow Corning Fluid 556.

The compositions of the present invention may be used to replace hydrosilation reaction systems using platinum catalysts and dual resin systems. The metathesis reaction is a homo-reaction using a single resin system, which simplifies the formulation, for example using the NBE-functionalized PDMS resins in combination with a ruthenium carbene complex catalyst. The resins of the present invention enable easy formulation of RTV materials, for example, a material similar to RTV6428 (GE Silicones, Waterford, N.Y.), as set forth in Example 4 below, because the viscosity range and working time characteristics are similar to those materials.

EXAMPLE 4

A Resin 7 was formulated to provide similar properties to that of the commercial RTV silicon marketed by GE, referred to as RTV6428. While RTV6428 is mixed with a 1:1 base/catalyst ratio, Resin 7 was mixed with a 10:1 ratio. The telechelic polydimethylsiloxane end-capped with norbornenylethyl groups (Compound 1) of Example 1 was used in the base paste, with n=243. The base paste formulation is provided below in Table 2:

TABLE 2

Base Paste Composition wt. %

| End-capped PDMS, 1 | 71 |
| Hexamethyldisilazane treated Kaolin | 9 |
| Sub-micron hydrophobic Silica | 20 |
| Total | 100 |

The catalyst used in the catalyst paste is 1,3-dimesityl-4,5-dihydroimidazol-2-ylidene-substituted ruthenium carbene complex (B) obtained from Materia, Inc., Pasadena, Calif. The catalyst component was formulated by dissolving it in a partially phenol substituted polymethylsiloxane, in particular, Dow Corning Fluid 556. The catalyst paste formulation is provided in Table 3:

TABLE 3

Test Catalyst Paste Composition (wt. %)

| Dow Corning Fluid 556 | 36.05 |
| Calcium Silicate Wollastonite (2–10 μm) | 53.70 |
| Sub-micron Silica | 10 |
| Catalyst Complex B | 0.25 |
| Total | 100 |

The physical properties for Resin 7 and the commercial RTV6428 composition are provided in Table 4. Both compositions provide similar working time and set time, as well as tensile strength. The compositions have different elongation, hardness and tear strength, which may be attributed to the type of filler and the extent of filler loading.

TABLE 4

Physical Property Comparison of Short Working Time Silicones

|  | GE-RTV6428 | Resin 7 |
| --- | --- | --- |
| Mixing Ratio | 1:1 | 10:1 |
| Viscosity of Base (Pa · s) | 0.88 | 19.6 |
| Working Time WT (sec) | 94 | 88 |
| Set time ST (sec) | 163 | 200 |
| Tensile Strength (MPa) | 3.57 | 3.47 |
|  | (0.30) | (0.40) |
| Elongation (%) | 85 | 244 |
|  | (6) | (16) |
| Hardness, Shore A | 62 | 37 |
| Tear Strength (N/mm) | 3.3 | 5.49 |
|  | (0.4) | (0.06) |

Using retarding additives in the formulation, it is believed that long working times up to several hours can be achieved at room temperature. Also, other retarding additives may be used to allow deactivation only below 120° C. to enable the composition's uses as an LSR material. The effectiveness of particular retarders is investigated further in commonly-owned, co-pending application Ser. No. 10/430,592, filed on even date herewith, and entitled METATHESIS-CURABLE COMPOSITION WITH A REACTION CONTROL AGENT.

Potential uses for compositions of the present invention include automotive applications, electric/electronics applications, electro and appliances, medical applications, textile applications, and other miscellaneous applications. By way of example and not limitation, automotive applications may include: distributor caps, cable bushings, loudspeaker covers, housing seals, bellows, plug seals, spark plug boots, vent flaps, grommets for weather packs, central door locker membranes, o-rings, gaskets, bushings, boots, and combined elements with thermoplastics. By way of example and not limitation, electric/electronics applications may include: sockets for antennas, terminals, plug connections, conductors (overvoltage), insulators (high voltage), housing seals, reinforced insulating hoses, vibration dampers (collectors), switch membrane covers (damp room switches), watch seals, insulating parts for hot adhesive guns, key pads for computers and telephones, anode caps, insulators and surge arresters, diaphragms, grommets, cable seals, and covers for switches; and castings, dielectrics and adhesives used in electronic applications such as those used in the semiconductor packaging industry. By way of example and not limitation, electro and appliance applications may include: small seals, cable bushings, reinforced insulating hoses, lamp seals, appliance feet, membranes, o-rings, diffuser for hair dryers, gaskets for faucets, gaskets for pressure cookers, detergent seals for dish washers, parts for coffee and espresso machines, coated glass fiber hoses for electric stoves, and water diffuser for shower bath. By way of example and not limitation, medical applications may include: seals for medical appliances, syringe plungers, breast nipple protectors, base plates (dental), inflating bellows, catheters, instrument mats, sterilization mats, o-rings for dialysers, earplugs, pipette nipples, catheter holders, cannula protection sleeves, nose clamps, valves and bellows for respirators, baby bottle nipples, baby pacifiers, stoppers, respiratory masks, Foley catheters, electrodes, parts for dental applications, and parts for medical equipment. By way of example and not limitation, textile applications may include: textile coating for conveyor belts, tents, compensators and technical applications, sleeves for electrical and heat insulation, heat reflecting fabrics for steel worker's coats, airbag coating, and printing inks. By way of example and not limitation, miscellaneous applications may include: swimming goggles, snorkels and mouthpieces for snorkels, elements for sport shoes, diving masks, swimming caps, respiratory devices, photocopier rolls and butcher's gloves. All of the foregoing are intended to be exemplary uses for the compositions of the present invention and are not intended to limit the invention in any way.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept.

What is claimed is:

1. A curable composition comprising:
    an olefin-containing resin system comprising at least one oligomer or polymer having a backbone of >50% linear siloxane units, the oligomer or polymer functionalized with olefin groups capable of undergoing a metathesis reaction, wherein the at least one oligomer or polymer 7. The composition of claim 1 wherein the resin system includes polydimethylsiloxane tethered and end-capped with norbornenylethyl groups and having the formula:

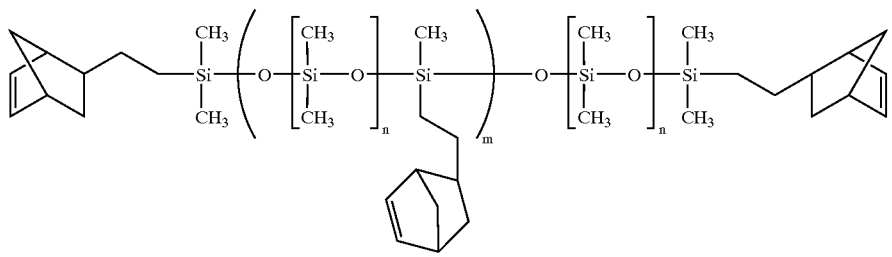

is selected from the group consisting of: an oligomer or polymer tethered and end-capped with the groups, a tri-functional oligomer or polymer end-capped with the groups, and a quadri-functional oligomer or polymer end-capped with the groups; and a ruthenium carbene complex catalyst capable of initiating the metathesis reaction in the composition to form a cured article, wherein the catalyst is selected from the group consisting of:

(a) a 1,3-bis-(2,4,6-trimethylphenyl)-2-(imidazolidinylidene) dichloro(o-isopropoxyphenyl-methylene) ruthenium catalyst having the structure:

E wherein R is mesityl; and (b) a catalyst having the structure:

wherein Cy is cyclohexyl, Ph is phenyl and X is a saturated imidazole ligand having a basicity higher than tricyclohexylphosphine.

2. The composition of claim 1 wherein the resin system includes polydimethylsiloxane tethered and end-capped with norbornenyl groups and having between about 5 and about 5000 dimethylsiloxane units.

3. The composition of claim 2 wherein the polydimethylsiloxane includes between about 27 and about 1590 dimethylsiloxane units.

4. The composition of claim 1 wherein the groups capable of undergoing a metathesis reaction are cycloalkenyl groups.

5. The composition of claim 1 wherein the groups capable of undergoing a metathesis reaction are norbornenyl groups.

6. The composition of claim 1 wherein the groups capable of undergoing a metathesis reaction are norbornenylethyl groups.

where n=5–5000, and m=1–100.

8. The composition of claim 1 wherein the resin system includes polydimethylsiloxane tethered and end-capped with cycloalkenyl groups.

9. The composition of claim 1 further comprising a silicone-based sulfosuccinate compound for accelerating the catalyst.

10. The composition of claim 1 further comprising a dimethicone copolyol sulfosuccinate ammonium salt for accelerating the catalyst.

11. The composition of claim 1 further comprising an ethoxylated alkylphenol surfactant.

12. A curable composition comprising:

an olefin-containing resin system comprising at least one oligomer or polymer having a backbone of >50% linear siloxane units, the oligomer or polymer functionalized with olefin groups capable of undergoing a metathesis reaction, wherein the at least one oligomer or polymer is norbornenyl functionalized quadri-functional polydimethylsiloxane; and a ruthenium carbene complex catalyst capable of initiating the metathesis reaction in the composition to form a cured article, wherein the catalyst is selected from the group consisting of:

(a) a 1,3-bis-(2,4,6-trimethylphenyl)-2-(imidazolidinylidene) dichloro(o-isopropoxyphenyl-methylene) ruthenium catalyst having the structure:

E wherein R is mesityl; and (b) a catalyst having the structure:

wherein Cy is cyclohexyl, Ph is phenyl and X is a saturated imidazole ligand having a basicity higher than tricyclohexylphosphine.

13. The composition of claim 1 wherein the resin system includes telechelic polydimethylsiloxane end-functionalized with norbornenylethyl groups and polydimethylsiloxane tethered and end-functionalized with norbornenylethyl groups.

14. The composition of claim 13 wherein the resin system further includes quadri-functional polydimethylsiloxane end-functionalized with norbornenylethyl groups.

15. The composition of claim 1 comprising a catalyst (b) of the formula:

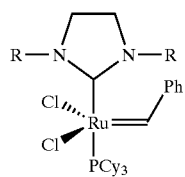

B wherein Cy is cyclohexyl, Ph is phenyl and R is mesityl.

16. The composition of claim 1 comprising a catalyst (b) of the formula:

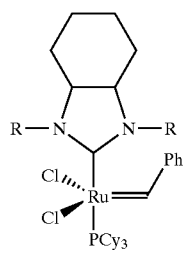

C wherein Cy is cyclohexyl, Ph is phenyl and R is mesityl.

17. The composition of claim 1 comprising a catalyst (b) of the formula:

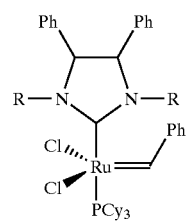

D wherein Cy is cyclohexyl, Ph is phenyl and R is mesityl.

18. A curable composition comprising:
an olefin-containing resin system comprising at least one oligomer or polymer having a polydimethylsiloxane backbone tethered and end-capped with cycloalkenyl groups capable of undergoing a metathesis reaction; and
a ruthenium carbene complex catalyst of the formula:

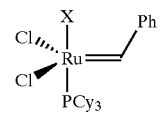

wherein Cy is cyclohexyl, Ph is phenyl and X is a saturated imidazole ligand having a basicity higher than tricyclohexylphosphine, and wherein the catalyst is capable of initiating the metathesis reaction in the composition to form a cured article.

19. The composition of claim 18 wherein the polydimethylsiloxane backbone includes between about 5 and about 5000 dimethylsiloxane units.

20. The composition of claim 18 wherein the polydimethylsiloxane backbone includes between about 27 and about 1590 dimethylsiloxane units.

21. The composition of claim 18 wherein the at least one oligomer or polymer includes polydimethylsiloxane tethered and end-capped with norbornenylethyl groups and having the formula:

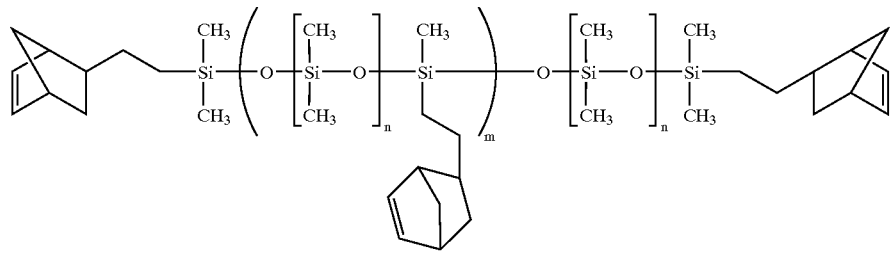

where n=5–5000, and m=1–100.

22. The composition of claim 18 further comprising a silicone-based sulfosuccinate compound for accelerating the catalyst.

23. The composition of claim 18 further comprising a dimethicone copolyol sulfosuccinate ammonium salt for accelerating the catalyst.

24. The composition of claim 18 further comprising an ethoxylated alkylphenol surfactant.

25. The composition of claim 18 wherein the resin system further includes norbornenylethyl functionalized quadri-functional polydimethylsiloxane.

26. The composition of claim 18 wherein the resin system further includes telechelic polydimethylsiloxane end-functionalized with norbornenylethyl groups.

27. The composition of claim 26 wherein the resin system further includes quadri-functional polydimethylsiloxane end-functionalized with norbornenylethyl groups.

28. The composition of claim 18 wherein the catalyst is a 4,5-dihydroimidazol-2-ylidene-substituted ruthenium carbene complex.

29. The composition of claim 18 wherein the catalyst is of the formula:

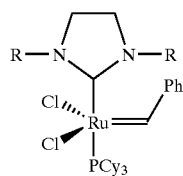

B wherein Cy is cyclohexyl, Ph is phenyl and R is mesityl.

30. The composition of claim 18 wherein the catalyst is of the formula:

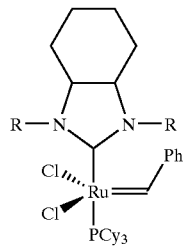

C wherein Cy is cyclohexyl, Ph is phenyl and R is mesityl.

31. The composition of claim 18 wherein the catalyst is of the formula:

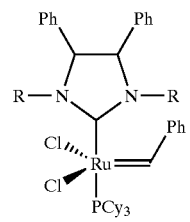

D wherein Cy is cyclohexyl, Ph is phenyl and R is mesityl.

32. A curable composition comprising:

an olefin-containing resin system comprising at least one oligomer or polymer having a polydimethylsiloxane backbone tethered and end-capped with cycloalkenyl groups capable of undergoing a metathesis reaction; and a 1,3-bis-(2,4,6-trimethylphenyl)-2-(imidazolidinylidene) dichloro(o-isopropoxyphenylmethylene) ruthenium catalyst having the structure:

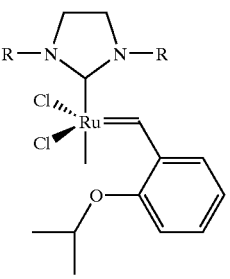

E wherein the catalyst is capable of initiating the metathesis reaction in the composition to form a cured article.

33. The composition of claim 32 wherein the polydimethylsiloxane backbone includes between about 5 and about 5000 dimethylsiloxane units.

34. The composition of claim 32 wherein the polydimethylsiloxane backbone includes between about 27 and about 1590 dimethylsiloxane units.

35. The composition of claim 32 wherein the at least one oligomer or polymer includes polydimethylsiloxane tethered and end-capped with norbornenylethyl groups and having the formula:

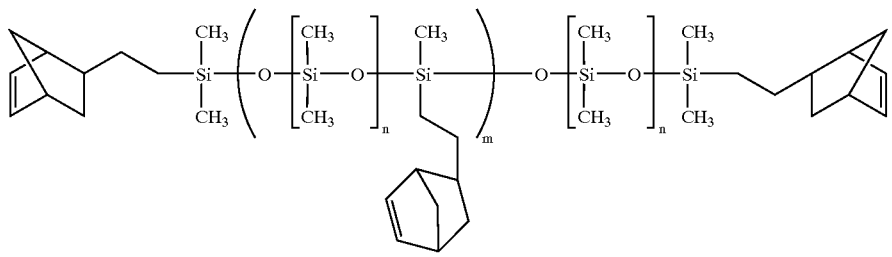

where n=5–5000, and m=1–100.

36. The composition of claim 32 further comprising a silicone-based sulfosuccinate compound for accelerating the catalyst.

37. The composition of claim 32 further comprising a dimethicone copolyol sulfosuccinate ammonium salt for accelerating the catalyst.

38. The composition of claim 32 further comprising an ethoxylated alkylphenol surfactant.

39. The composition of claim 32 wherein the resin system further includes norbornenylethyl functionalized quadri-functional polydimethylsiloxane.

40. The composition of claim 32 wherein the resin system further includes telechelic polydimethylsiloxane end-functionalized with norbornenylethyl groups.

41. The composition of claim 40 wherein the resin system further includes quadri-functional polydimethylsiloxane end-functionalized with norbornenylethyl groups.

* * * * *

UNITED STATES PATENT AND TRADEMARK OFFICE
CERTIFICATE OF CORRECTION

PATENT NO. : 6,844,409 B2
DATED : January 18, 2005
INVENTOR(S) : Angeletakis et al.

It is certified that error appears in the above-identified patent and that said Letters Patent is hereby corrected as shown below:

Title page,
Item [56], References Cited, OTHER PUBLICATIONS, "Chevaller" should be -- Chevalier --.

Column 1,
Line 15, "tiled" should read -- filed --.

Column 4,
Line 62, "$C_{16}$" should read -- $C_{18}$ --.

Column 8,
Line 37, "H—Si—O—H" should read -- HO—Si—O—H --.

Column 11,
Line 17, "wt. %" should read -- (wt. %) --.

Column 12,
Line 1, "uses" should read -- use --.

Signed and Sealed this

Twenty-third Day of August, 2005

JON W. DUDAS
*Director of the United States Patent and Trademark Office*